United States Patent [19]
Coyle et al.

[11] Patent Number: 5,099,046
[45] Date of Patent: Mar. 24, 1992

[54] METHOD FOR MAKING $Mo_4S_4L_6$ (C-2387)

[75] Inventors: Catherine L. Coyle, Mendham; Peter J. Guzi, Lambertville, both of N.J.; Thomas R. Halbert, Baton Rouge, La.; Edward I. Stiefel, Bridgewater, N.J.

[73] Assignee: Exxon Research and Engineering Company, Florham Park, N.J.

[21] Appl. No.: 703,219

[22] Filed: May 20, 1991

[51] Int. Cl.$^5$ .............................................. C07F 11/00
[52] U.S. Cl. ....................................... 556/61; 556/13; 556/15; 556/57; 252/33.6
[58] Field of Search ....................... 556/61, 57, 13, 15; 252/33.6; 260/414

[56] References Cited

U.S. PATENT DOCUMENTS

| | | | |
|---|---|---|---|
| 4,483,762 | 11/1984 | Grosboll | 556/61 X |
| 4,727,165 | 2/1988 | Kukes et al. | 556/57 |
| 4,832,877 | 5/1989 | Bino et al. | 556/61 X |
| 4,889,647 | 12/1989 | Rowan et al. | 556/61 X |
| 4,927,966 | 5/1990 | Kalman | 556/61 X |

Primary Examiner—Arthur C. Prescott
Attorney, Agent, or Firm—Joseph J. Dvorak

[57] ABSTRACT

The present invention provides an improved method for preparing compounds of the formula $Mo_4S_4L_6$ comprising:

contacting a compound having the formula $Mo_2S_4L_2$, wherein L is a 1,1-dithioacid ligand, with a reducing agent having a reduction potential sufficient to reduce Mo(V) to lower oxidation states, especially to Mo(III) and Mo(IV), at a temperature and for a time sufficient to form the $Mo_4S_4L_6$ compound. Preferably, the $Mo_2S_4L_2$ compound is dissolved in an organic solvent along with the reducing agent and the solution is heated at temperatures above 25° C., up to the boiling point of the solvent and, more preferably, at temperatures in the range of from about 50° C. to about 250° C.

13 Claims, No Drawings

METHOD FOR MAKING $Mo_4S_4L_6$ (C-2387)

FIELD OF THE INVENTION

This invention relates to improvements in the synthesis of $Mo_4S_4L_6$ compounds.

BACKGROUND OF THE INVENTION

Molybdenum compounds having a thiocubane structure are produced by a variety of methods. For example, T. Shibahara et al, *J. Am. Chem. Soc.*, Vol. 106, pp. 789–791 (1984) discusses a method for making the $[Mo_4S_4(edta)_2]3-$ion containing species by reacting a water soluble Mo(V) dimer in HCl. P. Kathirgamanathan et al, *J. Chem. Soc., Chem. Commun.*, pp. 953–954 (1985), describes electrochemically reducing a $Na_2[Mo(V)_2S_2O_2(cysteine)_2]\cdot 3H_2O$ in HCl to form $(Me_4N)_5[Mo_3S_4(NCS)_9]$ and the tetramer $(Me_4N)_7[Mo_4S_4(NCS)_{12}]$. P. Kathirgamanathan et al, *J. Chem. Soc., Chem. Commun.*, pp. 1437–1439 (1985), describes preparing mixtures of $(Me_4N)_5[Mo_3X_4(NCS)_9]$ and $(Me_4N)_7[Mo_4X_4(NCS)_{12}]$ compounds, where X is sulfur or oxygen. More recently, in U.S. Pat. No. 4,990,271 there is described a method for making thiocubane Mo compounds having the formula $Mo_4S_4(ROCS_2)_6$ by reacting molybdenum hexacarbonyl, $Mo(CO)_6$, with a xanthogen disulfide.

Notwithstanding the plethora of methods for preparing molybdenum containing thiocubane type compounds, there remains a need for a preparative method that is more simple and less expensive.

It is, therefore, an object of the present invention to provide an improved method for forming thiocubane Mo compounds of the general formula $Mo_4S_4L_6$, where L is a dithioacid ligand.

SUMMARY OF THE INVENTION

Accordingly, there is provided an improved method for preparing compounds of the formula $Mo_4S_4L_6$ comprising:

contacting a compound having the formula $Mo_2S_4L_2$, wherein L is a 1,1-dithioacid ligand with a reducing agent having a reduction potential sufficient to reduce Mo(V) to lower oxidation states, especially to Mo(III) and Mo(IV), at a temperature and for a time sufficient to form the $Mo_4S_4L_6$ compound. Preferably, the $Mo_2S_4L_2$ compound is dissolved in an organic solvent along with the reducing agent and the solution is heated at temperatures above 25° C., up to the boiling point of the solvent and, more preferably, at temperatures in the range of from about 50° C. to about 250° C.

DETAILED DESCRIPTION

In a preferred method of the present invention, a compound having the formula $Mo_2S_4L_2$, wherein L is a 1,1-dithioacid ligand, is added to a sufficient amount of an organic solvent to form a solution.

In general, any dithioacid ligand may be used. Thus, L may be a dithiocarbamate, xanthate, thioxanthate, dithiophosphate, dithiophosphinate, or other similar dithioacids and mixtures thereof. Preferably, the ligands, L, will have organo groups having from about 1 to 30 carbon atoms. For example, when L is a dithiocarbamate, $(S_2CNR_2-)$, or a xanthate, $(S_2COR-)$ the organo group R preferably will have from 1 to 30 carbon atoms.

The $Mo_2S_4L_2$ compound can be prepared by generally known techniques.

Any organic solvent capable of dissolving the $Mo_2S_4L_2$ compound may be used in the method of this invention. Preferably, the organic solvent chosen will also be capable of dissolving the reducing agent used in the process. In general, hydrocarbons, ethers and formamides are useful. Especially useful are organic solvents that have boiling points above about 50° and in the range, for example, of from about 50° C. to about 250° C. Indeed, aromatic hydrocarbons, such as toluene or xylene, or other solvents, such as tetrahydrofuran, dimethylformamide and mixtures thereof are most preferred organic solvents for use in this invention.

Thus, a solution of the $Mo_2S_4L_2$ compound and the reducing agent is prepared. The reducing agent may be any compound with a reduction potential sufficient to reduce the Mo(V) in the $Mo_2S_4L_2$ compound to a lower oxidation state, such as Mo(III) and Mo(IV). Suitable reducing agents include Zn, Mg, $NaBH_4$, dithionite salts, $LiR_3BH$, $R_4NBH_4$, where R is an alkyl group containing 1 to about 30 carbon atoms, and mixtures thereof.

The mole ratio of reducing agent to $Mo_2S_4L_2$ compound employed will range generally from about 0 10 to about 100 and, preferably, from about 0.25 to about 10.

Optionally but preferably, a disulfide of a 1,1-dithioacid is added to the solution of the $Mo_2S_4L_2$ compound and reducing agent. In general, from about 0.1 to about 10 moles of disulfide per mole of dimer is added and, preferably, about 2 moles of disulfide per mole of $Mo_2S_4L_2$ compound. The additional disulfide improves the yield obtained in converting the $Mo_2S_4L_2$ compound to the $Mo_4S_4L_6$ compound. Also, the disulfide of the dithioacid added to the solution preferably is a disulfide of xanthates, dithiocarbamates, dithiophosphates, dithiophosphinates and the like.

In yet another embodiment of the invention, a salt of any of the 1,1-dithioacids, L, previously mentioned can be added to the solution of the $Mo_2S_4L_2$ compound and reducing agent. Typical salts include alkali metal, alkaline earth metal, ammonium and alkylammonium salts. In general, these will be added in amounts ranging from about 0.1 to 10 moles of salt per mole of $Mo_2S_4L_2$ compound and, preferably, about 0.5 to about 2 moles per mole of $Mo_2S_4L_2$ compound.

After forming the solution, as outlined above, in some instances a reaction may occur at ambient temperature and heating of the reactants will be unnecessary. In general, however, the solution is heated at a temperature and for a time sufficient to form the $Mo_4S_4L_6$ compound. Typically, the solution will be heated at a temperature above room temperature up to the boiling point of the solvent. More typically, the solution will be heated at temperatures in the range of from about 50° C. to about 250° C. The time of heating will depend upon a number of factors, such as the reducing agent, the solvent and the temperature employed. In general, however, the solution will be heated for times ranging between about 0.5 hours to about 24 hours or more.

The $Mo_4S_4L_6$ product can be isolated readily from the heated solution by any number of well known techniques. In some instances, the product will precipitate from solution and, hence, can be separated and recovered by filtration. In other instances, the solvent can be removed, for example, in vacuo, and the crude product will remain. The crude product can, of course, be purified by recrystallization, column chromatography or the like.

The following examples will serve to illustrate specific procedures used in accordance with the claimed invention.

EXAMPLE 1

Synthesis of $Mo_4S_4[(C_4H_9)_2NCS_2]_6$ by Reduction with $NaBH_4$ $Mo_2S_4[((C_4H_9)_2NCS_2]_2$ (50 mg, 0.7 mmol) and tetraisobutylthiuramdisulfide (14 mg, 0.35 mmol) were dissolved in dimethylformamide (4 ml), forming a solution. The solution was combined with a sodium borohydride (10 mg, 0.094 mmol) solution in 4 ml DMF and heated to 120° C. for 1 hour. A purple colored $Mo_4S_4[(C_4H_9)_2NCS_2]_6$ was recovered in 35% yield by silica column chromatography using a solution of 75% $CH_2Cl_2$:25% hexane as the eluent.

EXAMPLE 2

Synthesis of $Mo_4S_4[(C_4H_9)_2NCS_2]_6$ by Reduction with $LiEt_3BH$ $Mo_2S_4[(C_4H_9)_2NCS_2]_2$ (100 mg, 0.14 mmol) was dissolved in tetrahydrofuran (7 ml) and degassed. Next, 0.15 ml of a 1 M solution of $LiBEt_3H$ in tetrahydrofuran (0.15 mmol) was added with a syringe to the $Mo_2S_4[(C_4H_9)_2NCS_2]_2$ solution. The resulting solution was stirred for 30 minutes and $Mo_4S_4[(C_4H_9)_2NCS_2]_6$ was recovered from solution in 12%-15% yield by silica column chromatography using a solution of 75 vol. % $CH_2Cl_2$ and 25 vol. % hexane as the eluent.

EXAMPLE 3

Synthesis of $Mo_4S_4[(C_8H_{17})_2NCS_2]_6$ by Reduction with $NaBH_4$ $Mo_2S_4[(C_8H_{17})_2NCS_2]_2$ (50 mg, 0.052 mmol) and sodium borohydride (8 mg, 0.075 mmol) were dissolved in dimethylformamide (4 ml) and heated to 120° C. for hour. The $Mo_4S_4[(C_8H_{17})_2NCS_2]_6$ compound (purple in color) was identified in the solution by thin layer chromatography.

EXAMPLE 4

Synthesis of $Mo_4S_4[(C_8H_{17})_2NCS_2]_6$ by Reduction with $NaBH_4$ in the Presence of $Na[(C_8H_{17})_2NCS_2]$ $Mo_2S_4[(C_8H_{17})_2NCS_2]_2$ (50 mg, 0.052 mmol) and the sodium salt of dioctyldithiocarbamic acid (8 mg, 0.024 mmol) were dissolved in dimethylformamide (3 ml) and added to the sodium borohydride (8 mg, 0.075 mmol) in 2 ml of dimethylformamide. The mixture was heated to 120° C. for 1 hour. A purple $Mo_4S_4[(C_8H_{17})_2NCS_2]_6$ formed and was identified in the solution by thin layer chromatography.

EXAMPLE 5

Synthesis of $Mo_4S_4[(C_8H_{17})_2NCS_2]_6$ by Reduction with $NaBH_4$ in the Presence of Tetraoctylthiuram Disulfide $Mo_2S_4[(C_8H_{17})_2NCS_2]_2$ (50 mg, 0.052 mmol), tetraoctylthiuram disulfide (17 mg, 0.027 mmol) and sodium borohydride (8 mg, 0.024 mmol) were heated together at 100° C. in dimethylformamide (5 ml) for 1 hour to form a solution. A 40% yield of purple $Mo_4S_4[(C_8H_{17})_2NCS_2]_6$ was recovered from the solution by silica column chromatography using a $CH_2Cl_2$ eluent.

EXAMPLE 6

Synthesis of $Mo_4S_4[(C_3H_7)_2NCS_2]_6$ by Reduction with $[(C_4H_9)_4NBH_4]$ in the Presence of Tetrapropyl Thiuram Disulfide $Mo_2S_4[(C_3H_7)_2NCS_2]_2$ (100 mg, 0.15 mmol), tetrapropyl thiuram disulfide (105 mg, 0.30 mmol) and tetrabutylammonium borohydride (191 mg, 0.59 mmol) were heated together at 115° C. in toluene (20 ml) for 4 hours. A 10% yield of purple $Mo_4S_4[(C_8H_{17})_2NCS_2]_6$ was recovered from the solution by silica column chromatography using $CH_2Cl_2$ as the eluent.

What is claimed is:

1. A method for making a compound having the formula $Mo_4S_4L_6$ comprising:
   contacting a compound having the formula $Mo_2S_4L_2$, wherein L is a 1,1-dithioacid ligand, with a reducing agent having a reduction potential sufficient to reduce Mo(V) to lower oxidation states, the contacting being conducted at a temperature and for a time sufficient to form the $Mo_4S_4L_6$ compound.

2. The method of claim 1 wherein the contacting is conducted in a solution.

3. The method of claim 2 wherein the ratio of reducing agent to $Mo_2S_4L_2$ compound is in the range of from about 0.10:1 to about 100:1.

4. The method of claim 3 wherein the reducing agent is selected from the group consisting of Zn, Mg, $NaBH_4$, $LiR_3BH$, $R_4NBH_4$ where R is an alkyl group of from 1 to about 30 carbon atoms, dithionite salts and mixtures thereof.

5. The method of claim 4 wherein the solution is heated at a temperature above about 25° C. to about 250° C.

6. The method of claim 5 wherein the reducing agent is $NaBH_4$.

7. The method of claim 5 wherein the reducing agent is $LiR_3BH$.

8. The method of claim 5 wherein the reducing agent is $R_4NBH_4$.

9. The method of claim 5 including adding a disulfide of a 1,1-dithioacid to the solution in amounts ranging from about 0.1 to about 10 moles of disulfide per mole of $Mo_2S_4L_2$.

10. The method of claim 5 including adding a salt of a 1,1-dithioacid to the solution in amounts ranging from about 0.5 to about 2 moles of salt per mole of $Mo_2S_4L_2$ compound.

11. The method of claim 9 wherein the ligand, L, of the $Mo_2S_4L_2$ compound and the disulfide of the 1,1-dithioacid are selected from the group consisting of dithiocarbamates, xanthates, thioxanthates, dithiophosphates, dithiophosphinates or mixtures thereof.

12. The method of claim 10 wherein the salt of the 1,1-dithioacid is selected from alkali, alkaline earth, ammonium, alkylammonium salts and mixtures thereof.

13. The method of claim 11 wherein the ligand and the 1,1-dithioacid are dithiocarbamates.

* * * * *